United States Patent
Inman et al.

(10) Patent No.: US 6,541,522 B2
(45) Date of Patent: Apr. 1, 2003

(54) METHODS OF USING COMPOSITIONS CONTAINING HYPOTRIGLYCERIDEMICALLY ACTIVE STILBENOIDS

(75) Inventors: Wayne D. Inman, Belmont, CA (US); David C. Hopp, Mill Creek, WA (US)

(73) Assignee: Insmed Incorporated, Glen Allen, VA (US)

( * ) Notice: Subject to any disclaimer, the term of this patent is extended or adjusted under 35 U.S.C. 154(b) by 0 days.

(21) Appl. No.: 09/920,304

(22) Filed: Aug. 2, 2001

(65) Prior Publication Data

US 2002/0055541 A1 May 9, 2002

Related U.S. Application Data

(60) Provisional application No. 60/225,704, filed on Aug. 16, 2000.

(51) Int. Cl.[7] .......................... A01N 37/10; A61K 31/19
(52) U.S. Cl. ........................................ 514/568; 514/576
(58) Field of Search ............................. 514/569, 576, 514/568; 562/475

(56) References Cited

U.S. PATENT DOCUMENTS 5,827,898 A 10/1998 Khandwala et al. ........ 514/734

FOREIGN PATENT DOCUMENTS

| WO | WO 99/56737 A1 | 11/1999 |
| WO | WO 00/30665 A1 | 6/2000 |
| WO | WO 01/74753 A1 | 10/2001 |
| WO | WO 02/13809 A2 | 2/2002 |
| WO | WO 02/13811 A2 | 2/2002 |
| WO | WO 02/14252 A2 | 2/2002 |

OTHER PUBLICATIONS

"3–Hydroxy–5–methoxystilbene–2–carboxylic acid, a phytotoxic compound isolated form methanolic extracts of pigeionpea (Cajanus Cajan Millsp.) leaves" Ohwaki et al. Soil Sci. Plant Nutr. (Tokyo) vol. 39(1), pp. 55–61. (1993).*
"Inhibitors of the Arachidonate Cascade from Allium chinense and Their Effect on in vitro Platelet Aggregation" Goda et al. Chem. Pharm. Bull. vol. 35(7), pp. 2668–2674 (1987).*
"Effects of Certain Indian Pulses on the Serum, Liver and Aortic Lipid Levels in Rats Fed a Hypercholesterolaemic Diet" Devi et al. Atherosclerosis, vol. 11, pp. 479–484. (1970).*
"Effects of Stilbene Components of the Roots of Poygonum cuspidatum Sieb. et Zucc. on Lipid Metabolism" Arichi et al. Chem. Pharm. Bull. vol. 30(5), pp. 1766–1770. (1982).*
"Inventory of Plants Used in Traditional Medicine in Tanzania. Part III. Plants of the Families Papilionaceae–vitaceae" Hedberg et al. J. of Ethnopharmacology. vol. 9, pp. 237–260. (1983).*

(List continued on next page.)

*Primary Examiner*—Mukund J. Shah
*Assistant Examiner*—Zachary C. Tucker
(74) *Attorney, Agent, or Firm*—Sterne, Kessler, Goldstein & Fox PLLC

(57) ABSTRACT

The use of isolated or purified stilbenoid compounds including longistyline A-2-carboxylic acid as a dietary supplement to mammals suffering from elevated triglyceride levels is described. The invention also relates to the use of such stibenoid compounds in combination with other hypotriglyceridemic agents.

12 Claims, 4 Drawing Sheets

OTHER PUBLICATIONS

"Anithyperlipidemic Effect of Flavonoids from *Pterocarpus marsupium*" Jahromi et al. J. of Natural Products, vol. 56 No. 7, pp. 989–994. (1993).*

"Comparative Study of Radical Scavenger and Antioxidant Properties of Phenolic Compounds From Vitis Vinifera Cell Cultures using In Vitro Tests" Fauconneau et al. Life Sciences, vol. 61 No. 21, pp. 2103–2110. (1997).*

"Structure–Requirements of Isocoumarins, Phthalides, and Stilbenes from Hydrangea Dulcis Folium for Inhibitory Activity on Histamine Release from Rat Peritoneal Mast Cells" Matsuda et al. Bioorganic and Medicinal Chemistry 7, pp. 1445–1450. (1999).*

"Two Novel Stilbene–2–Carboxylic Acid Phytoalexines From *Cajanus cajan*" Cooksey et al, Phytochemistry, vol. 21(12), pp. 2935–2938 (1982).* del Olmo, E., et al., "Anti–Trypanosoma Activity of Some Natural Stilbenoids and Synthetis Related Heterocyclic Compounds," *Bioorg. Med. Chem. Lett. 11*:2755–2757, Elsevier Science, Ltd. (Oct. 2001).

Mitscher, L.A., et al., "Amorfrutin A and B, bibenzyl anti-microbial agents from *Amorpha fruticosa,*" *Phytochemistry 20*:781–786, Pergamon Press, Ltd. (1981).

Panlasigui, L.N., et al., "Glycaemic response in normal subjects to five different legumes commonly used in the Philippines," *Int. J. Food Sci. Nutr. 46*:155–160, Journals Oxford, Ltd. (1995).

Prema, L., and Kurup, P.A., "Effect of protein fractions from *Cajanus cajan* (Redgram) and *Dolichos biflorus* (Horsegram) on the serum, liver, and aortic lipid levels in rats fed a high–fat–high–cholesterol diet," *Atherosclerosis 18*:369–377, Elsevier Scientific Publishing Company, Amsterdam (1973).

Prema, L., and Kurup, P.A., "Hypolipidaemic Activity of the Protein Isolated from *Cajanus cajan* in High Fat–cholesterol Diet Fed Rats," *Indian J. Biochem. Biophys. 10*:293–296, Indian Publications And Information Directorate Csir (1973).

Dialog File 351, Accession No. 1988–004858, Derwent WPI English language abstract for JP 62270529 A.

International Search Report for International Application No. PCT/US01/25383 mailed Jun. 25, 2002.

Bhattacherjee, P., et al., "The Effects of a Novel Series of Selective Inhibitors of Arachidonate 5–Lipoxygenase on Anaphylactic and Inflammatory Responses," *Ann. N.Y. Acad. Sci. 524*:307–320, New York Acadamy of Sciences (1988).

Goda, Y., et al., "Inhibitors of the Arachidonate Cascade from *Allium chinense* and Their Effect on in Vitro Platelet Aggregation," *Chem. Pharm. Bull. 35*:2668–2674, Pharmaceutical Society of Japan (1987).

Gowri, M.S., et al., "Masoprocol decreases rat lipolytic activity by decreasing the phosphorylaton of HSL," *Am. J. Phsiol. Endocrinol. Metab. 279*:E593–E600, American Physiological Society (Sep. 2000).

Gryglewski, R.J. and Eckstein, M., "Fibrinolytic Activity of some Biarylcarboxylic Acids," *Nature 214*:626, Macmillan Journals Ltd. (1967).

Pending Non–Provisional U.S. patent application No. 09/919,995, Inman et al., filed Aug. 2, 2001.

* cited by examiner

METHODS OF USING COMPOSITIONS CONTAINING HYPOTRIGLYCERIDEMICALLY ACTIVE STILBENOIDS

CROSS-REFERENCE TO RELATED APPLICATION

This application claims priority to U.S. Provisional Application Ser. No. 60/225,704, filed Aug. 16, 2000.

BACKGROUND OF THE INVENTION

1. Field of the Invention

The present invention relates to stilbenoids that exhibit hypotriglyceridemic activity in mammals. Provided herein are processes for obtaining such stilbenoids, particularly from *Cajanus cajun;* compositions comprising the stilbenoids and methods for their use in dietary supplements for administration to mammals suffering from elevated serum triglyceride levels and for normalizing serum triglyceride levels.

2. Related Art

Uses of Cajanus SPP

Plants of Cajanus spp. (Leguminoseae), particularly *C. cajun,* also known as pigon pea or redgram, are herbaceous members of the family Leguminoseae that grows widely throughout Africa, Asia and South and Central America. Cajanus spp. have been used in traditional medicine to treat stomach aches for women suspected of being pregnant, to treat wounds and scalds, to treat toothache, against gonorrhoea, to treat bad vison; and against heart diseases (Hedberg, H, et al., J Ethnopharmacol, 9 (2/3), 237–260 (1983).

In addition to its use by traditional healers, these plants may also be included in the normal diet as a food plant. Canjanus spp are consumed by people in India, especially those of the lower economic levels. To that end, studies have reported that rats fed redgram, blackgram and horsegram exhibited a lipid lowering effect.(Saraswathi Devi, K., et al., Atherosclerosis, 11, 479 (1970)).

Extracts from various Leguminosae plants have been reported to exhibit hypotriglyceridemic activity. Jahromi reported a hypolipedemically active ethylacetate fraction extracted from a hypolipedemically active aqueous decoction of *Pterocarpus marsupium* (Leguminosae). Jahromi, M. A. F, et al., J. Nat. Prods. 56(7), 989–994 (1993). Investigations have also reported an active hypertriglyceridemic agent of redgram contained in an extracted protein (globulin) fraction. Prema, L., et al., Atherosclerosis 18, 369–277 (1973). Prema, L., et al., Indian J. Biochem. Biophys., 10, 293–296 (1973).

While extracts of the genus Cajanus have been used medicinally, such use is not without potential drawbacks. First, in addition to containing one or more compounds having a "desired" biological activity, plant materials often contain a myriad of naturally-occurring organic compounds among which one or more can elicit a physiological or pharmacological response that contraindicate use for the desired activity. Secondly, when administered in the form of a plant extract, the actual dosage of the unknown active compound(s) is impossible to regulate, which can result in an ineffective amount, i.e., too low or too high a concentration, of active compound administered.

Thus, there remains a need for an isolated or a purified, hypoglycemically, hypotriglyceridemically active compound, compositions comprising effective amounts of such a compound and methods for their use.

Isolated Stilbenoids

The term stilbenoid refers to stilbenes, bibenzyls (7,8-dihydrostilbenes) and phenyldihydroisocoumarins together with a number of nitrogen free phenatlirenols, which are thought to be products of the same metabolic pathway that leads to stilbenes. Gorham, J., *The Stilbenoids* in *Progress in Phytochemistry,* Vol. 6, Reinhold, et al., eds., Pergamon Press, New York, 1980, pp 203–252. Stilbenes (7,8-dihydrostilbenes) generally have two stereoisomeric forms, a trans- or a cis-skeleton:

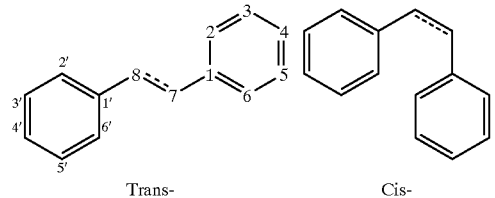

Trans-　　　　　　　Cis-

Generally, naturally occurring stilbenes and bibenzyls are hydroxy and/or methoxy substituted at the 3,3',4,4',5, and 5' positions. Some naturally occurring stilbenes and bibenzyls include pinosylvin (3,5-dihydroxy stilbene), piceatannol (3,3',4,5'-tetrahydroxystilbene), piceid (3,4',5-trihydroxystilbene-3-O-β-D-glucopyranoside) and resveratrol (3,4'5-trihydroxystilbene). Mono-(3-hydroxy-5-methoxystilbene) and di-methyl (3,5-dimethoxystilbene) ethers of trans-pinosylvin and their respective dihydroderivatives have been reported isolated from the heartwood of *Pinus armandi, P. morrisonicola,* and *P. parviflorai.* Fang, J-M, et al., Phytochemistry 27(5): 1395–1397 (1988).

Stilbenoids may also be prenylated or homogeranylated at the 2 and 4 (4 and 6) positions. 4-isopentenylresveratrol (3,4',5-trihydroxy-4-(3-methyl-2-butenyl)stilbene) was isolated from *Arachis hypogea* (Keen, N. T., et al., Phytochemistry 15, 1794 (1976)). A prenylated pinosylvin dimethyl ether (3,5-dimethoxy-4-(3-methyl-2-butenyl)stilbene) was isolated from *Derris rariflora* (Braz Filho, R., et al., Phytochemistry 14, 261 (1975a)) and *D. floribunda* (Braz Filho, R., et al, Phytochemistry 14, 1454 (1975b)). A prenylated resveratrol trimethyl ether (3,4',5-trimethoxy-4-(3-methyl-2-butenyl)stilbene) was also reported isolated from *D. floribunda* (Braz Filho, R., et al., 1975b). Chlorophorin (4-homogeranyl-2,3',4,5'-tetrahydoxystilbene) was isolated from *Chlorophora excelsa* (Grundon, M. F., et al., Nature (Lond.) 163, 154 (1949)). The occurrence in plants of isoprenice chains substituted stilbenes has also been reported by King and Grundo (J. Chem. Soc. 1950, 3547 (1950)), Cooksey (Cooksey, C. J., et al., Phytochemistry 21(12), 2935 (1982)) and Monache (Lloydia 40(2): 201–208 (1977)).

Stilbenoid-2-carboxylic acid derivatives have been isolated from various plants. Hydrangeic acid (3,4'-dihydroxystilbene-2-carboxylic acid) was reported isolated from the common garden hydrangea (*Hydrangeqa macrophylla*) Pryce, R. J., Phytochemistry 10, 2679 (1971). A glycoside, gaylussacin, reported isolated from *Gaylussacia frondosa,* and *G. vassata* (Ericaceae), produced a 3,5-dihydroxystilbene-2-carboxylic acid derivative (gaylussacin aglycone). Askari, A., et al., Lloydia 35,49 (1972).

Stilbenoids Isolated from Cajanus spp.

Four isoprenylated stilbene 2-carboxylic acid phytoalexins (3-hydroxy-5-methoxy-6-(3-methyl-2-butenyl) stilbene-2-carboxylic acid, 3-hydroxy-5-methoxy-4-(3-methyl-2-butenyl)stilbene-2-carboxylic acid, 3,5-dimethoxy-6-(3-methyl-2-butenyl)stilbene-2-carboxylic acid, and 3,5- dimethoxy-4-(3-methyl-2-butenyl)stilbene-2-carboxylic acid) were reported isolated from the leaves of *Canjanus cajan* challenged with *Botrytis cinerea* (Cooksey, C J, et al., Phytochemistry 21(12):2935–2938 (1982).

Biological Activity of Stilbenoids

Various biological activites have been reported of the stilbenoids. For example, cis-piceid; trans-, cis-resveratrol, astringin and astringinin from *Vitis vinifera* were tested for antioxidant activities (A. Fauconneau, B., et al., Life Sci. 61(21): 2103 (1997)). 3,3',4,5'-tetrahydroxystilbene was reported to have strong antifungal activity (Inamori, Y., et al., Chem. Phar. Bull. 33(7):2904–09 (1985)). Resveratrol has also been reported to exhibit antiplatelet aggregation activity. Chung, M-I, et al., Planta Med. 1992 58:274–275; and Kimura, Y., et al., Biochim. Biophys. Acta 1995 175, 275–278); coronary vasodilator activity (Inamori, Y., et al., Chem. Pharm. Bull. 35, 887–89 (1987), anti-leukemia activity (Mannila, E., Phytochemistry, 1003, 33, 813–816), antifungal activity (Lanagcake, P., et al., Phytochemistry 1979, 18, 1025–1027; Hart, J. H/., et al. Phytopathology 1979 69:1138–1143) and protein-tyrosine kinase inhibitory activity (Orsini, F., et al., J. Nat. Prods. 60 1082–1087 (1997)).

The antitriglyceridemic activity of stilbenoids has also been investigated. Piceid (3,4',5-trihydroxystilbene-3-O-β-D-glucopyranoside) isolated from the roots of *Polygonum cuspidatium* (also known as "Kojo-kon" and "Itadori-kon") has been reported to lower serum triglyceride and liver lipid levels. Arichi H., et al., Chem. Pharm. Bull. 30(5) 1766–1770 (1982). 2,3,5,4'-tetrahydroxy stilbene-2-O-D-glucoside isolated from *Polygonum multiflorum* has also been reported to reduce serum triglyceride levels. Arichi, H, et al., 1982.

Inventors are not aware, of any prenylated or 2-carboxylic acid stilbenoids reported to exhibit antihypertriglyceridemic activity. Inventors are not aware, however, of any stilbenoids isolated from Cajanus spp reported to exhibit antihypertriglyceridemic activity.

Citation or identification of any reference described herein shall not be construed as an admission that such reference is available as prior art to the present invention.

SUMMARY OF THE INVENTION

The present invention provides compositions comprising a hypotriglyceridemically effective amount of an isolated compound of the formula:

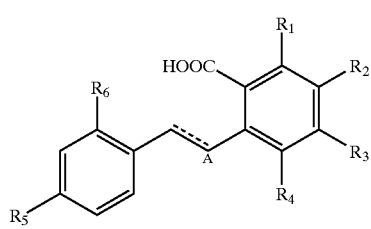

(I)

wherein
  A is a bond selected from the group consisting of a single bond and a double bond in trans conformation, as noted by ---;
  $R_1$ and $R_3$ are independently selected from the group consisting of H, OH, and $C_{1-6}$alkoxy;
  $R_2$ and $R_4$ are independently selected from the group consisting of H, $C_{1-10}$alkyl, $C_{2-10}$alkenyl, and $C_{2-10}$alkynyl;
  $R_5$ and $R_6$ are independently selected from the group consisting of H, OH, and $C_{1-6}$alkoxy;
  or pharmaceutically acceptable salts thereof.

The present invention also provides methods to reduce blood triglyceride levels in a mammal comprising administration of a composition of the present invention. The compositions of the present invention are useful to treat hypertriglyceridemia in mammals.

DETAILED DESCRIPTION OF THE INVENTION

Definitions

Figure 1:
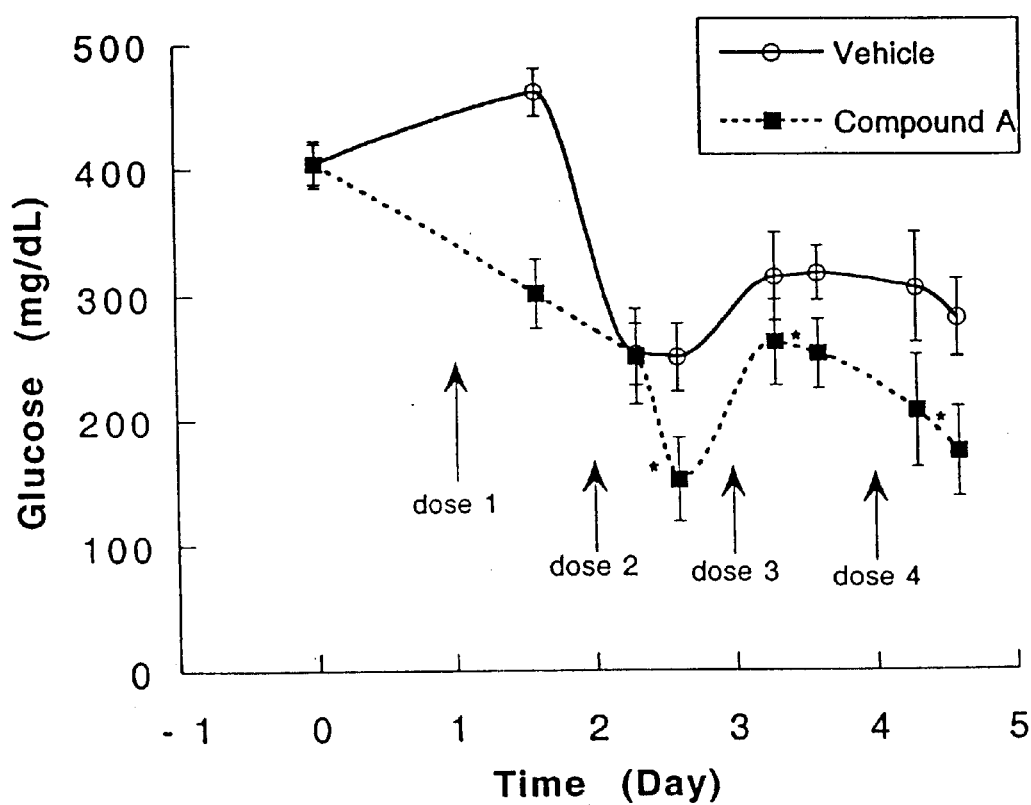
FIG. 1 is a line graph showning mean serum glucose levels in Fat feed Streptozotocin (STZ) treated rats administered with GELUCIRE vehicle only (2.5 mL/kg), and Compound A (250 mg/kg qd). -O- represents vehicle; and -■- represents Compound A. Blood was sampled six hours post-dose on day 2 and three and six hours post-dose on days 2 to 4. N=8 in all cases.

As used herein, the term "independently" or the equivalents thereof is employed to described an instance were two or more groups may be the same or different from each other and the occurrence of one group does not impact or influence the occurrence of the other group.

The term "alkyl" refers to a monovalent alkane (hydrocarbon) derived radical containing from 1 to 10 carbon atoms unless otherwise defined. It may be straight or branched. Preferred straight or branched alkyl groups include methyl, ethyl, propyl, isopropyl, butyl, 3-butyl, and t-butyl. Alkyl also includes a straight or branched alkyl group that contains or is interrupted by a cycloalkylene portion.

The term "cycloalkyl" refers to cyclic monovalent alkanes. Preferred cycloalkyl groups include cyclopentyl and cyclohexyl.

The term "alkenyl" refers to a hydrocarbon radical straight or branched containing from 2 to 10 carbon atoms and at least one carbon to carbon double bond. Preferably one carbon to carbon double bond is present, and up to four non-aromatic (non-resonating) carbon—carbon double bonds may be present. Preferred alkenyl groups include ethenyl, propenyl, butenyl and geranyl.

The term "alkynyl" refers to a hydrocarbon radical straight or branched containing from 2 to 10 carbon atoms and at least one carbon to carbon triple bond. Up to three carbon—carbon triple bonds may be present. Preferred alkynyl groups include ethynyl, propynyl and butynyl.

The term "alkoxy" represents an alkyl group of indicated carbon atoms attached through an oxygen linkage.

Hypotriglyceridemically Active Stilbenoids

The present invention provides compositions comprising a hypotriglyceridemically effective amount of an isolated compound of the formula:

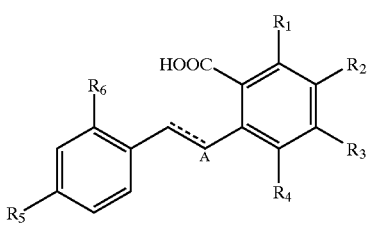

(I)

wherein
A is a bond selected from the group consisting of a single bond and a double bond in trans conformation;
$R_1$ and $R_3$ are independently selected from the group consisting of H, OH, and $C_{1-6}$alkoxy;
$R_2$ and $R_4$ are independently selected from the group consisting of H, $C_{1-11}$alkyl, $C_{2-11}$alkenyl, and $C_{2-11}$alkynyl;
$R_5$ and $R_6$ are independently selected from the group consisting of H, OH, and $C_{1-6}$alkoxy;
or a pharmaceutically acceptable salt thereof.

The following define embodiments of the present invention in more detail:
$R_1$ is preferably H, OH, methoxy, or ethoxy;
$R_2$ is preferably $C_{1-11}$ alkyl or $C_{2-11}$ alkenyl. In a particular embodiment, $R_2$ is $C_{1-6}$ alkyl or $C_{2-6}$ alkenyl. $R_2$ is most preferably 3-methyl-2-butenyl or 3-methylbutyl;
$R_3$ is preferably H, OH, methoxy, or ethoxy;
$R_4$ is preferably $C_{1-11}$ alkyl or $C_{2-11}$ alkenyl. In a particular embodiment, $R_4$ is $C_{1-6}$ alkyl or $C_{2-6}$ alkenyl. R4 is most preferably 3-methyl-2-butenyl or 3-methylbutyl.

In one embodiment of the present invention are compositions comprising a hypotriglyceridemically effective amount of an isolated compound having the formula:

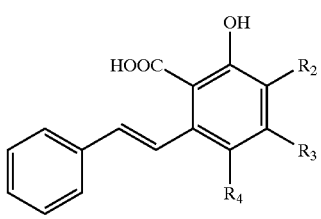

wherein,
$R_2$ and $R_4$ are selected from the group consisting of H, $C_{1-11}$ alkyl or $C_{2-11}$ alkenyl and either $R_2$ or $R_4$ are H; and
$R_3$ is $C_{1-6}$ alkoxy.

Preferred compounds of formula (I) are selected from the group consisting of:

(A) 3-hydroxy-4-(3-methyl-2-butenyl)-5-methoxystilbene-2-carboxylic acid (Compound A);

(B) 3-hydroxy-6-(3-methyl-2-butenyl)-5-methoxystilbene-2-carboxylic acid (Compound B);

(C) 4-(3-methyl-2-butenyl)-3,5-dimethoxystilbene-2-carboxylic acid (Compound C);

(D) 6-(3-methyl-2-butenyl)-3,5-dimethoxystilbene-2-carboxylic acid (Compound D);

(E) 3,4'-dihydroxystilbene-2-carboxylic acid (Compound F);

(F) 3,5-dihydroxystilbene-2-carboxylic acid (Compound F);

(G) 3,4'-dihydroxybibenzyl-2-carboxylic acid (Compound G);

(H) 3,5-dihydroxy-4-(3-methyl-2-butenyl)bibenzyl-2-carboxylic acid (Compound H); and (I) 3,5-dihydroxy-4-(3-methyl-2-butenyl)bibenzyl-2-carboxylic acid (Compound I).

Specific Embodiments of the Present Invention

The following compounds illustrate the structure and nomenclature of the compounds of Formula (I) and other compounds described herein.

Compound A

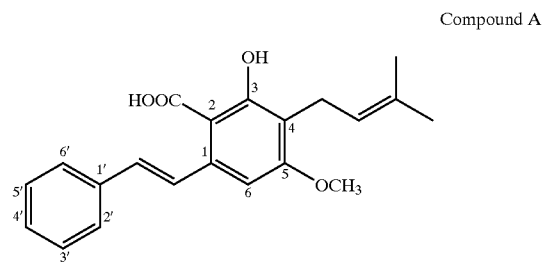

Compound A may also be known as longistyline A-2-carboxylic acid; 3-hydroxy-4-isoprenyl-5-methoxystilbene-2-carboxylic acid; 3-hydroxy-4-(3-methyl-2-butenyl)-5-methoxystilbene-2-carboxylic acid; 2-hydroxy-4-methoxy-3-(3-methyl-2-butenyl)-6-(trans-styryl)benzoic acid and 3-methoxy-4-(3-methyl-2-butenyl)-5-(trans-styryl)phenol.

Compound B

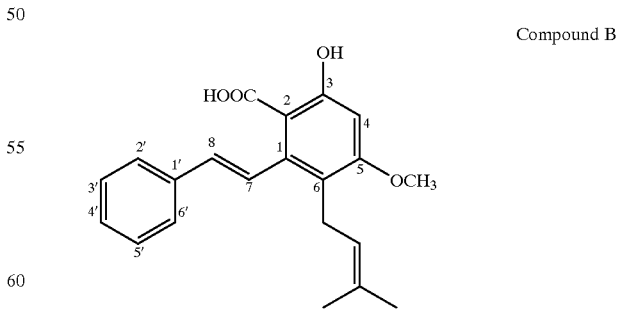

Compound B may also be known as 3-hydroxy-6-isoprenyl-5-methoxystilbene-2-carboxylic acid; or 3-hydroxy-5-methoxy-6-(3-methyl-2-butenyl)stilbene-2-carboxylic acid.

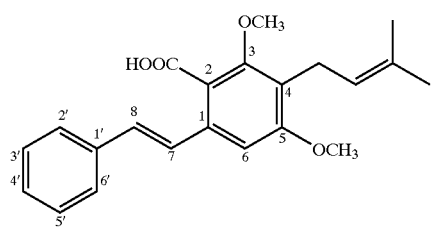

Compound C

Compound C may also be known as 3,5-dimethoxy-4-isoprenylstilbene-2-carboxylic acid; or 3,5-dimethoxy-4-(3-methyl-2-butenyl)stilbene-2-carboxylic acid.

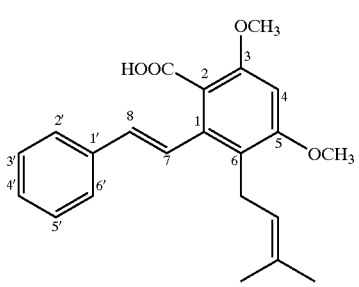

Compound D

Compound D may also be known as longistylene C-2-carboxylic acid; 3,5-dimethoxy-6-isoprenylstilbene-2-carboxylic acid; or 3,5-dimethoxy-6-(3-methyl-2-butenyl)stilbene-2-carboxylic acid.

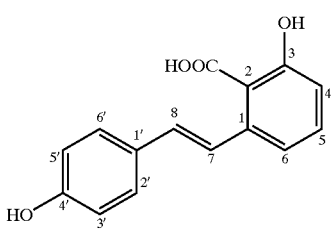

Compound E

Compound E may also be known as hydrangeic acid, or 3,4'-dihydroxystilbene-2-carboxylic acid.

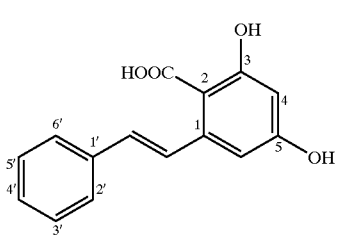

Compound F

Compound F may also be known as gaylussacin aglycone; or 3,5-dihydroxystilbene-2-carboxylic acid.

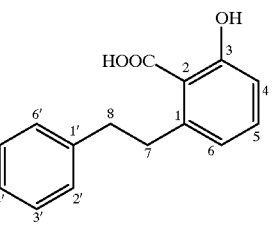

Compound G

Compound G may also be known as lunularic acid; 3,4'-dihydroxybibenzyl-2-carboxylic acid; or 3,4'-dihydroxy-7,8-dihydrostilbene-2-carboxylic acid.

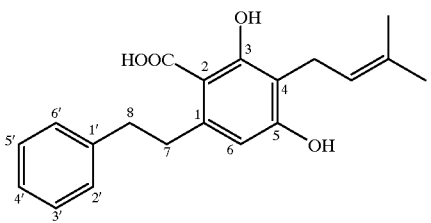

Compound H

Compound H may also be known as 3,5-dihydroxy-4-(3-methyl-2-butenyl)bibenzyl-2-carboxylic acid; 3,5-dihydroxy-4-isoprenylbibenzyl-2-carboxylic acid; 3,5-dihydroxy-4-(3-methyl-2-butenyl)-7,8-dihydrostilbene-2-carboxylic acid; or 3,5-dihydroxy-4-isoprenyl-7,8-dihydrostilbene-2-carboxylic acid.

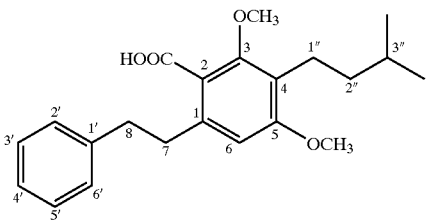

Compound I

Compound I may also be known as 7,8,2",3"-tetrahydrolongistyline A-2-carboxylic acid; 4-isopentyl-3,5-dimethoxybibenzyl-2-carboxylic acid; 1-(3,5-dimethoxy-4-[3-methyl-2-butyl])phenol-4-phenolethane.

Processes for Isolating Stilbenoids

The Compounds A–D can be isolated directly from Cajanus spp., preferably from *C. cajun*, or chemically synthesized and isolated from a reaction mixture. Compounds E–I can be isolated or semi-synthesized by methods known by those of skill in the art and also as described herein. By whatever manner, the isolated stilbenoids of formula (I) can be obtained in purified form, preferably in substantially purified form, via column chromatography, recrystallization or other means known to those skilled in the art.

Isolating Stilbenoids from *Cajanus SPP*

Compounds A–D can be isolated from Cajanus spp., preferably *C. cajun* using the illustrative methods described below or other standard extraction and purification techniques known to those of ordinary skill in the art (Cooksey, C. J., et al., 1982).

Isolating Stilbenoids from other Species

Compound E has been reported isolated from *Hydrangea macrophylla* (Gorham, J., Phytochemistry 16, 249 (1977)). The glycoside of Compound F, gaylussacin, was reported isolated from the leaves of *Gaylussacia baccata*, and *G. frondosa* (Askari, A., Lloydia, 35(1), 49 (1972)). Compound G (lunularic acid) has been isolated from *Hydrangea macrophylla* (Valio, I F M, et al., Nature (London) 223, 1176 (1969), Gorham, J., Phytochemistry 16, 249 (1977) and Pryce, R. J., Phytochemistry 10, 2679 (1971). Compound H was reported identified in *Radula complanata*; and Compound I was semi-synthesized from Compound H by methylation with $(Me)_2SO_4$. Asakawa, Y., et al., Phytochemistry 17, 2115 (1978). Methylation of acidic bibenzyls can be attained with $(Me)_2SO_4$. Asakawa (1978).

Isolating and Purification of Stilbenoids

Plant material from Cajanus spp., preferably *C. cajun* (Leguminoseae) is initially extraced with a solvent to provide a crude extract containing the identified stilbenoids. By "plant material" is meant any part of the Cajanus plant, such as bark, leaves, flowers, roots and stems. Preferably, the leaves of the Cajanus plant are utilized. The plant material may optionally be shredded, ground, macerated, or otherwise treated prior to extraction. Alternatively, the plant material may already be in a powdered, shredded, ground, macerated, or comminuted state when used herein. Suitable extraction solvents include polar solvents, non-polar solvents, or mixtures thereof. Useful polar solvents include, but are not limited to, acetonitrile, methanol, ethanol, isopropanol, acetone, butanol, ethyl acetate, tetrahydrofuran, dimethylformamide, N-methylpyrrolidinone, dimethyl sulfoxide, water and mixtures thereof. Useful non-polar solvents include pentane, hexane, heptane, higher alkane and other hydrocarbon solvents, such as petroleum ether.

Preferably, the plant material is extracted with a polar solvent, so as to maximize the amount of stilbenoids that can be extracted from the plant material. More preferably, the plant material is washed with a mixture of polar solvent and water, wherein the ratio of water to polar solvent ranges from 1:99 to 99:1 volume/volume (v/v). Most preferably, the polar solvent is an organic alcohol, such as methanol, ethanol, isopropanol, acetone, butanol and the like. When the organic alcohol is ethanol, the ratio of water to organic alcohol is preferably about 5:95 to about 95:5 (v/v), more preferably from about 10:90 to about 30:70 (v/v) and most preferably about 20:80 (v/v).

Extracting the plant material with solvent can be performed at a temperature of about room temperature to about the reflux temperature of the chosen solvent or solvent system, preferably at room temperature, for between about 2 hours and 72 hours, preferably for between about 24 hours, in order to maximize the amount of stilbenoids that can be isolated from the plant material.

The plant material may also be agitated, soaked-or otherwise exposed to the solvent to facilitate the extraction process. For example, the plant material can be mechanically mixed, sonicated, or otherwise agitated in the solvent by methods known by those skilled in the art.

The resulting crude extract can then filtered to remove undesired solid impurities therefrom and to afford a crude filtrate containing the stilbenoids. Suitable filtering methods include passing the crude extract through diatomaceous earth, e.g., CELITE™ (diatomaceous earth sold by Fisher Scientific (Los Angeles, Calif.)), CELATOM™ (diatomaceous earth sold by Great Western Chemical of Richmond, Calif.); silica gel; or a fritted funnel. Centrifugation of solutions or diluted solutions of the crude extract can also be employed to remove undesired solid impurities therefrom.

The crude filtrate is concentrated, preferably in vacuo, and the resulting residue further purified by being partitioned between two partitioning solvents, so as to enhance the yield and overall purity of the isolated stilbenoids. It is important that the partitioning solvents are immiscible in each other. Preferably, one of the partitioning solvents is a non-aqueous solvent such as benzene, toluene, diethyl ether, ethyl methyl acetate, chloroform, carbon tetrachloride, acetate, pentane, hexane, heptane, higher alkane (C<7) solvents, dichloromethane and other hydrocarbon solvents, such as petroleum ether, known by those skilled in the art to be immiscible in water or capable of dissolvating stilbenoids. The aqueous solvent should preferably be capable of dissolving impurities found in the plant material.

The organic phase, containing the stilbenoids, is separated, optionally combined, and then concentrated to dryness to afford a crude concentrate, which is enriched in stilbenoids. The previously described extraction and filtering steps can be repeated to increase the yield and overall purity of the isolated stilbenoids. The crude concentrate can be further purified by standard techniques known to those skilled in the art to ultimately afford isolated stilbenoids. Exemplary purification techniques include recrystallization and chromatography. Preferably, the crude concentrate is purified using liquid chromatography, for example high performance liquid chromatography, vacuum flash chromatography and adsorption chromatography.

Various resin types can be utilized to achieve the desired chromatographic effect. For example, in order to remove polar impurities therefrom, the crude concentrate can be passed through an adsorption resin (HP-20, C-18, or silica gel) to selectively retain or pass the stilbenoids according to polarity. Size, molecular weight, or cellulosic characteristics of the desired resin material may be used to separate the stilbenoids by selective use of molecular exclusion or cellulose based resins.

An appropriate gradient solution is used to wash and separate the stilbenoids from the crude concentrate on the column filled with the desired resin. A suitable gradient may include an initial wash of a solvent followed by an elution solvent. Suitable elution solvents contain a high percentage of acetonitrile (ACN), methanol, acetone, dichloromethane, ether/hexane or any other organic solvent or mixtures thereof that can release stilbenoids from the resin material, and into an enriched fraction. The enriched fraction will be stilbenoids, or mixtures thereof. The elution solvent can contain up to 50% water, so as to adjust or optimize the polarity thereof. The type of elution solvent can depend upon the type of resin used. For example, for HP-20 resin equilibrated in methanol, the elution solvent can be dichloromethane; for C-18 resin equilibrated in 70% ACN/30% water (v/v), a gradient of increasing acetonitrile concentration is appropriate; or for silica gel resin equilibrated in hexane, the elution solvent can be a gradient of increasing ether in a ether/hexane concentration solution.

High performance liquid chromatography (HPLC), thin layer chromatography (TLC) and nuclear magnetic resonance (NMR) analysis can be used to determine which of the eluting fractions is an enriched fraction, and which enriched fractions contain the desired stilbenoids. Optionally, different eluting fractions can be combined and subjected to the TLC and NMR analyses described above. The enriched fractions can optionally be repurified using either the same or a different eluent system.

The resulting fractions containing the stilbenoids are concentrated, optionally in vacuo. The fractions containing the stilbenoids from the chromatography methods described above can be combined and further purified by successive iterations of the above, or by recrystallization or other types of chromatography. Optionally, successive recrystallization or chromatography purifications may be performed to obtain purified stilbenoids.

Using the above purification techniques, the isolated stilbenoids can be purified or substantially purified. By "substantially purified" is meant that the stilbenoids of formula (I) have a degree of purity of at least about 95%. By "purified" is meant that the stilbenoids of formulae (I), (II) and (III) have a degree of purity of at least about 97%.

Organic Synthesis of the Stilbenoids of Formula (I)

There are two main methods for synthesizing stilbenoids, the earliest being variations on the Perkin condensation of a phenylacetic acid with a benzaldehyde to form a stilbene-$\alpha$-carboxylic acid, followed by decarboxylation. Funk, C, et al., Chem. Ber., 38, 939 (1905); Buckles, R. E., et al., J. Am. Chem. Soc. 73, 4972 (1951); and Letcher, R. M., Phytochemistry 12, 2789 (1973). Moreover, the Wittig reaction between a benzyltriphenyl-phosphonium chloride or a diethylbenzylphosphonate and a benzaldehyde has been used to give a higher yield of a predominantly trans-stilbene. Gorham, J., Phytochemistry, 16, 249 (1977); Wheeler, O. H., et al., J. Org. Chem. 30, 1473 (1965). Bibenzyls are also readily prepared from stilbenes by catalytic hydrogenation with hydrogen in the presence of palladium on carbon.

The compounds of formula (I) may also be semi-synthesized from other isolated stilbenoids. 3-hydroxy-5-methoxy-4-isoprenylstilbene-2-carboxyolic acid (Compound A) and 3-hydroxy-5-methoxy-6-isoprenylstilbene-2-carboxylic acid (Compound B) were reported isolated from *Cajanus cajun* (Cooksey, C. J., et al, (1982)). Methylation of these compounds with diazomethane gave 3,5-dimethoxy-6-isoprenylstilbene-2-carboxylic acid and 3,5-dimethoxy-4-isoprenylstilbene-2-carboxylic acid, respectively. Cooksey, C J, et al. (1982). Hydrolyzing the glycoside gaylussacin with emulsion produced Compound E, the gaylussacin aglycon. Askari, A., et al. (1972). Compound G, lunularic acid, has been obtained by the reduction of hydrangenol. Asahina, Y., et al., Ber-.dtsch.chem.Ges 63, 429 (1930).

Stilbene-2-carboxylic acids have also been synthesized. Lunularic acid has been obtained by the reduction of hydrangenol. Asahina, Y, et al., (1930). Other routes to obtain lunularic acid have been described by Arai, et al., Phytochemistry 12, 2279 (1973); Arai, Y., et al., Tetrahedron Lett. p 1615 (1972) and by Huneck, S., et al., Phytochemistry 16, 1013 (1977). Lunularic acid can also be synthesized by the Perkin condensation of a phenylacetic acid with a benzaldehyde to form a stilbene-$\alpha$-carboxylic acid. Letcher, R. M., et al, Phytochemistry 12, 2789 (1973). Na(4-hydroxyphenyl)acetate and 3-hydroxybenzaldehyde in Ac$_2$O, followed by hydrolysis with NaOH-EtOH under N$_2$, also produced lunularic acid. Gorham, J, (1977).

Lunularic acid may also be synthesized in vivo by a phenylpropanoid-polymalonate pathway. Pryce, R. J., Phytochemistry, 10, 2679 (1971).

Once the stilbenoids of formula (I)have been synthesized, they can be purified or substantially purified, using conventional chromatography, recrystallization or other purification techniques known to those skilled in the art.

Derivatives of Stilbenoids

Also included within the scope of the present invention are ether and acetate derivatives of stilbenoids that are useful for lowering serum triglyceride levels and treating hypertriglyceridemia. For example, the carboxylic acid groups of the stilbenoid-2-carboxylic acids can be methylated with CH$_2$N$_2$ and ether to produce the methyl ether thereof.

Eischer synthesized lunularic acid and some of their derivatives starting from the methylether or the acetate of ethyl 6-methyl-salicylate and introducing the bibenzyl moiety by metalation, alkylation or by bromination, Wittig reaction, and hydrogenation sequences. Eischer, T., et al., Synthesis, 525–529 (1988). In addition, the hydroxyl groups of these stilbenoids can be acetylated by methods well known to those skilled in the art, for example, using acetyl chloride (Greene, *Protective Groups in Organic Synthesis* 101, (1981)).

It is to be pointed out that any hydroxyl groups not so methylated or acetylated can participate in the formation of those pharmaceutically acceptable salts of stilbenoids described above.

Pharmaceutical Compositions of Stilbenoids of Formula (I)

The stilbenoids of formulae described herein may be compounded, for example with a pharmaceutically acceptable carrier for solid compositions such as tablets, pellets or capsules; capsules containing liquids; suppositories; solutions; emulsions; suspensions or any other form suitable for use. Suitable carriers include, for example, sterile water, sterile physiological saline, gum acacia, gelatin, starch paste, talc, keratin, colloidal silica, urea and the like. In addition, auxiliary, stabilizing, thickening, lubricating and coloring agents may be used. The stilbenoids of formulae described herein are present in the compositions in an amount sufficient to produce a desired effect upon diabetes, blood glucose levels; or hyperglycemia.

Compositions for oral administration may be in the form of tablets, troches, lozenges, aqueous or oily suspensions, granules or powders, emulsions, capsules, syrups or elixirs. Orally administered compositions may contain one or more agents, such, as sweetening agents such as fructose, aspartame or saccharin; flavoring agents such as peppermint, oil of wintergreen, or cherry, coloring agents and preserving agents to provide a pharmaceutically palatable preparation. Moreover, compositions in tablet form may be coated to delay disintegration and absorption in the gastrointestinal tract thereby providing a sustained action over an extended period of time. Selectively permeable membranes surrounding an osmotically active driving compound are also suitable orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monosterate or glycerol sterate may also be used.

Aqueous suspensions containing the stilbenoids of formulae described herein may also contain one or more preservatives, such as, for example, ethyl or n-propyl-p-hydroxy-benzoate, one or more coloring agents, flavoring agents or sweetening agents.

Dietary Supplements Containing Stilbenoids

The stilbenoids of formulae described herein can be used in the form of a food additive, food supplement, dietary supplement for example, in solid, semisolid or liquid form, which contains at least one of the stilbenoids of formulae described herein, including their therapeutically active salts, as a bioactive component. When incorporated into foodstuffs, the active stilbenoid may be used as an isolated compound or may be contained in an enriched fraction of plant extract.

The compounds of the present invention may be incorporated into foodstuffs alone or in combination with another antidiabetic, antihyperglycemic (blood glucose lowering), or anti-lipidemic compound, in admixture with a carrier or an excipient suitable for oral administration.

Compositions for oral administration may be in the form of foodstuffs comprising the compositions of this invention.

Any conventional food processing technique may be used to achieve a product comprising the effective amount of the stilbenoid compound of formula (I). There is much information on the art and technology of the various conventional food processing techniques and their practices in both the pet food and food industries, and it is accordingly assumed that the general principals of these techniques are understood by the person skilled in the art.

With the addition of a stilbenoid to a carrier material, the method of assimilating the stilbenoid compound is not limited to simple baking or dehydration, but may also include such techniques as extrusion processing, coextruding, and canning. Additionally, the process by which granola bars and food bars are prepared may be used to prepare the present foodstuffs. Thus, various types of food products may be produced in the practice of the invention in addition to powder ingredients for finished foods. For example, foodstuffs produced in the practice of the invention include dry pet foods that serve as a complete nutritional diet for pets, as well as biscuits and treats for pets. Additionally, the present foodstuffs may be formed into cereals, snacks, and nutrition bars for humans. Regardless of the method by which the present foodstuffs are prepared or the components therein, it is preferred that the resulting foodstuffs will provide a stilbenoid concentration of at least about 0.1 gram per dietary unit.

In the practice of the invention, the carrier material is contemplated to be a dry material of proteinaceous or farinaceous character. Nonexclusive examples of suitable carrier materials include: dried bakery product, the flours of wheat, rice, oat, corn, and soy; the brans of wheat, rice, oat, and corn; wheat middlings; whole ground wheat, corn gluten meal, whole ground corn, soybean meal, barley, sorghum, meat and bone meals, poultry meal, fish meal, dry dog food, and the like of the various materials that typify conventional commercial and premium pet food products.

The foodstuff produced in the practice of the invention may take any form that is edible by humans or pets, including a complete and balanced pet food; a dry or semi-dry product that is an additive for pet food or human food; or granola-type bars, nutrition bars or other snacks for humans. Specifically, if the foodstuff comprises a stilbenoid of formula (I), it is contemplated that it will be employed as an ingredient to be incorporated into another foodstuff. Toward that end, the stilbenoid can be in the form of a powder or fine meal that may then serve as an ingredient to other foods. Additional examples of foodstuffs contemplated for human consumption that may include, as an ingredient, stilbenoids processed in accordance with the invention include fillings or puddings (similar to gelatins and JELLO products), as well as performance foods in liquid gel form and canned soups.

Methods for use of Hypotriglyceridemically Active Stilbenoids

Due to the activity of the stilbenoids of the present invention, the stilbenoids of formulae described herein or pharmaceutically acceptable salts thereof are advantageously useful pharmaceutical compositions and dietary supplements. Such compositions and dietary supplements may be used to treat mammals suffering from high triglyceride levels, such as mammals with obesity or diabetes.

In one embodiment of the present invention the pharmaceutical compositions or dietary supplements are used to lower serum fatty acids in mammals with type I or type II diabetes.

In another embodiment of the present invention are methods using a stilbenoid of Formula I for use in the treatment of obesity in human or non-human animals.

As appropriate for the treatment of type I or type II diabetes or obesity, a composition of present invention may be administered which contains a stilbenoid of formulae described herein or a pharmaceutically or the acceptable salt thereof as described above, together with an antidiabetic, antihyperglycemic or blood glucose lowering agent including, but not limited to insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an alpha-glucosidase inhibitor such as acarbose or miglitol; a Pradrenoceptor agonist such as PL-316, 243, etc., cholestyramine, clofibrate, colestipol, fluvastatin, gemfibrozil, lovastatin, niacin, pravastatin, probucol, psyllium hydrophilic muccilloid, simvastatin, and sodium dichloroacetate. Alternatively, the compositions comprising a hypotriglyceridemically active stilbenoid or a pharmaceutically acceptable salt thereof can be administered in combination with, prior to, concurrent with or subsequent to the administration of another antidiabetic, antihyperglycemic, or anti-lipidemic agent as described supra.

In another embodiment of the present invention are methods for preventing, halting or slowing the progression of atherosclerotic cardiovascular diseases and related conditions and disease events and hypertension in human or non-human animals. In this embodiment, one may advantageously administer a stilbenoid of Formula I with at least one other compound that lowers serum triglyceride or chloresterol. Such compounds are well known in the art, and include, but are not limited to (A) fibrates; (B) HMG-CoA reductase inhibitors; and (C) inhibitors of cholesterol absorption; (D) squalene synthesis inhibitors; (E) LDL catabolism enhancers; and (F) angiotensin converting enzyme inhibitors.

Fibrate compounds are drugs having actions of lowering blood cholesterol levels by inhibiting synthesis and secretion of triglycerides in liver and activating a lipoprotein lipase. Examples of the fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, etc.

Statin compounds are drugs having actions of lowering blood cholesterol levels by inhibiting hydroxymethylglutalyl CoA (HMG-CoA) reductase. Examples of the statin compounds include pravastatin and its sodium salt, simvastatin, lovastatin, atorvastatin, fluvastatin, etc.

Squalene synthesis inhibitors are drugs having actions of lowering blood cholesterol levels by inhibiting synthesis of squalene. Examples of the squalene synthesis inhibitors include (S)-alpha-[Bis[2,2-dimethyl-1-oxopropoxy) methoxy]phosphinyl]-3-phenoxybenzenebutanesulfonic acid, mono potassium salt (BMS-188494).

LDL catabolism enhancers are drugs having actions of lowering blood cholesterol levels by increasing the number of LDL (low-density lipoprotein) receptors. Examples of the LDL catabolism enhancers include N-[2-[4-bis(4-fluorophenyl)methyl-1-piperazinyl]ethyl]-7,7-diphenyl-2,4,6-heptatrienic acid amide.

Angiotensin converting enzyme inhibitors are drugs having actions of partially lowering blood glucose levels as well as lowering blood pressure by inhibiting angiotensin converting enzymes. Examples of the angiotensin converting enzyme inhibitors include captopril, enalapril, alacepril, delapril, ramipril, lisinopril, imidapril, benazepril, ceronapril, cilazapril, enalaprilat, fosinopril, moveltopril, perindopril, quinapril, spirapril, temocapril, trandolapril, etc.

When administered to a mammal for veterinary use or to a human for clinical use, the stilbenoids of formulae described herein are administered in isolated form. By "isolated" is meant that the stilbenoids of formulae described herein are separated from other components of either (a) a natural source such as a plant or cell culture, or (b) a synthetic organic chemical reaction mixture. Preferably, via conventional techniques, the stilbenoids of formulae described herein are substantially purified, preferably purified.

When administered to a mammal for veterinary use or to a human for clinical use, the stilbenoids of formulae described herein can be used alone or in combination with any physiologically acceptable carrier or excipient suitable for enteral or parenteral administration. Where used for parenteral administration, the physiologically acceptable carrier must be sterile and suitable for in vivo use in a human, or for use in a veterinary clinical situation.

The compositions of this invention may be administered by a variety of methods including orally, intramuscularly, intravenously, subcutaneously, transdermally, rectally or by inhalation. While the preferred mode of administration is through the oral mode, the precise mode of administration is left to the discretion of the practitioner. They are advantageously effective when administered orally.

This invention comprises the use of a stilbenoid, preferably in isolated or purified form administered at a dose of about 1 to 1,000 mg per kg of body weight per day, preferably from about 2 to about 500 mg per kg of body weight per day, more preferably about 5 to about 350 mg per kg of body weight per day, still more preferably about 50 to about 350 mg per kg of body weight per day. In still a further embodiment, the invention comprises the use of a stilbenoid of formulae described herein at a dose of about 5 to about 350 mg/kg body weight/day of compound to be utilized in an amount which results in the compositions exhibiting a therapeutically effective hypoglycemic, antihyperglycemic or antidiabetic activity. The dosage of the present compositions for treatment or prevention of hypertriglceridemia or for reducing blood fatty acids levels, depends on the route and frequency of administration was well as the age, weight and physical condition of the patient. Generally the daily dosage is in the range of about 1 to 1,000 mg per kg of body weight per day, preferably from about 2 to about 500 mg per kg of body weight per day, more preferably about 5 to about 350 mg per kg of body weight per day, still more preferably about 50 to about 350 mg per kg of body weight per day. Treatment can be repeated as needed, depending upon the dosage and need, for example, a dosage of about 62.5, 125 or 250 mg/kg body weight/day of patient animal can be administered in dividing doses to prevent or treat diabetes or to lower blood fatty acid levels. Treatment can be continued, for example, reduced to the desired until the blood fatty acids concentration is near physiological, is stabilized at a desired level, or to be maintained at a desired level. The appropriate dosage of the compositions can be readily determined by the skilled medical practitioner.

The stilbenoids of formulae described herein can optionally be administered in an effective amount as pharmaceutically acceptable salt. Due to the prevalence of carboxyl and phenolate moieties, pharmaceutically acceptable carboxylate or phenolate salts may be generally recognized by one of ordinary skill in the are using, for example, counter ions such as sodium, potassium, lithium, calcium, magnesium, zinc and iron.

The following examples are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention incorporated herein.

EXAMPLES

Isolation and Characterization of Stilbenoid Solvent Extraction

Compounds, Materials and Methods

Analytical high performance liquid chromatography (HPLC) was performed on a Hitachi Model D-6500 Chromatography Data Station equipped with a L-6200A pump, AS-2000 autosampler, a L-4500 A diode array detector and a Sedex 55 light scattering detector connected in parallel, and a Primesphere C18 HC, 4×50 mm (5 $\mu$m) HPLC column. All chromatographic runs were performed at ambient temperature. HPLC grade solvents were used without further purification.

Nuclear magnetic resonance (NMR) spectra were recorded on a Varian Unity Plus 400 or a Varian Unity 400 spectrometer. NMR spectra of compounds were recorded in deuterated acetone. One and two-dimensional NMR experiments, including Distortionless Enhancement Polarization Transfer (DEPT), H—H Correlation Spectroscopy (COSY), Heteronuclear Multiple Quantum Correlation (HMQC), Heteronuclear Mutiple Bond Correlation (HMBC), long-range Heteronuclear Chemical Shift Correlation (HETCOR) provided molecular structure information. MS spectra were recorded on a Kratos MS-50 in high resolution power electron impact scanning mode, 70 ev. Resolution was set to 2000, scanning rate 10 sec/decay, temperature gradient from 50° to 300° C. increased at a rate of 50°/min. IR spectra were recorded on a Perkin-Elmer 1600 Series FTIR. UV spectra were recorded on a Perkin-Elmer Lambda 2 UV/VIS spectrometer or taken directly from the Hitachi diode-array UV detector on the HPLC system.

Isolation of Stilbene Compounds using Solvent Extraction

Ground leaf material of *Cajanus cajun* (11 kg) was stirred in 110 L of methanol for 24 hours with an overhead mixer (Scheme 1). Stirring was intermittent (5 minutes every 30 minutes during the day). The methanol solution was filtered through 1 kg of CELITE™, and evaporated in vacuo to give 1.39 kg of a green oily material. This material was triturated with 20 L of acetone for four hours. The acetone mixture was vacuum filtered through 1 kg of CELITE™ and the filtrate evaporated to dryness giving 721 g of solids. The solids (538 g) were placed in a 4 L beaker and stirred with 2 L of methanol for 30 minutes using a magnetic stirrer. After 30 minutes the supernatant was decanted. This procedure was repeated two more times, first with 2 L and finally 1 L of methanol. The methanol extracts were combined to give 4 L of solution to which 1 L of water was slowly added with mixing. The resulting milky suspension was pumped onto an 18×92 cm column containing HP 20 (Mitsubishi-Kasei) sorbent that had been washed previously with 40 L of acetone followed by 80 L of 4:1 methanol/water. An additional 1 L of 4:1 methanol/water was pumped onto the column. The column was eluted with 95:5 methanol/water. Fourteen 10 L fractions were collected. Fractions 7–10 were pooled and evaporated in vacuo giving 64 g of an oily solid. This material was dissolved into 6.5 L of methanol to which 3.5 L of water was added along with 10 mL of acetic acid. After 30 minutes the mixture was filtered through Whatman #2 filter paper. Both the methanol precipitation solids and methanol precipitation filtrate were kept for further processing.

Scheme 1

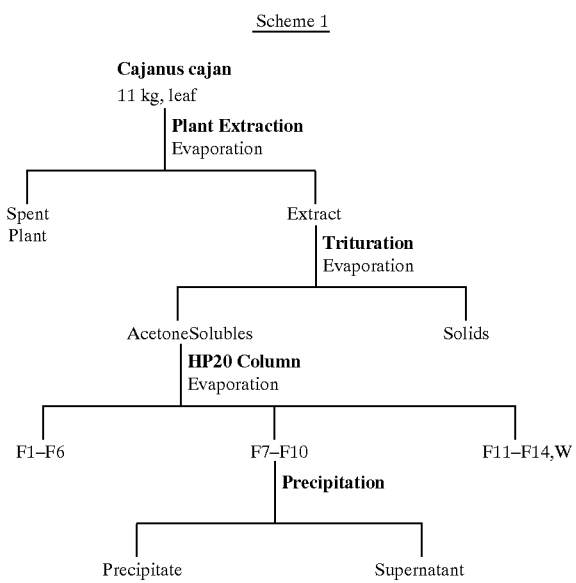

The methanol precipitation solids were dried in a vacuum oven overnight at 40° C. This gave 10 g of a white amorphous powder, which was placed into an Erlenmeyer flask along with 500 mL of n-hexane (Scheme 2). With good mixing, acetone was added until the solution became clear. One gram of decolorizing charcoal was added to the stirred solution, which was then vacuum filtered through a bed (2 g) of CELITE™ diatomaceous earth. The filtrate was allowed to stand open, in a hood, overnight resulting in the precipitation and generation of solids. The supernatant was decanted and 40 mL of hexane and 5 mL of acetone were added back to the solids, which formed two layers upon standing at for two hours. The layers were separated and the top layer was allowed to stand uncovered overnight, yielding colorless crystalline solids. The crystalline material was triturated with a minimal amount of 10:1 hexane/acetone, and allowed to stand in a closed container at room temperature overnight. The supernatant was decanted and the crystals dried in a vacuum oven giving 6 g of material, identified as Compound A from NMR and HPLC diode array data. Yield from plant was 0.07%.

Scheme 2

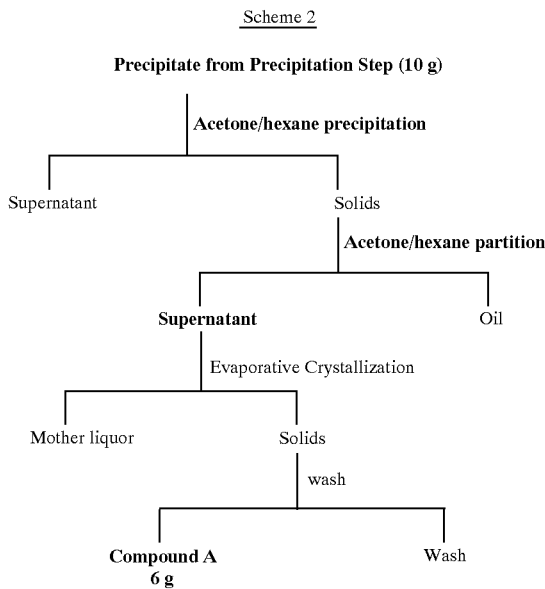

The methanol precipitation filtrate (10 L) was passed through a small amount of C-18 (Bakerbond, 40 mm) and pumped onto a 100×5 cm C-18 chromatography column which had been washed with methanol and equilibrated with 65:35:0.1 methanol/water/acetic acid (Scheme 3). An additional 500 mL of 65:35:0.1 methanol/water/acetic acid was pumped through the column in order to complete the loading. The column was eluted with 80:20:0.1 methanol/water/acetic acid. Thirty-two fractions, each containing 1 L, were collected. Fractions 12–18 were pooled and evaporated in vacuo to give 18 g of solids. The solids (11.1 g) were dispersed into 700 mL of hexane with stirring. To the dispersion was added enough dichloromethane (200 mL) to produce a clear solution. To this solution was added 1 g of decolorizing charcoal. The suspension was stirred for 1 hour then filtered through a bed of CELITE™ (39 g) diatomaceous earth. The CELITE™ diatomaceous earth bed was washed with an additional 100 mL of 7:2 hexane/dichloromethane. The combined solutions (1000 mL) were slowly (3 hr) evaporated using a stream of nitrogen to a volume of 300 mL. The solids were filtered, dried in a vacuum oven and recrystallized as follows. The dried material (8 g) was dissolved into 10 mL of dichloromethane to which was added 70 mL of hexane with stirring. The solution was allowed to stand uncovered until solids formed. The container was then covered and allowed to stand overnight at –10° C. The resulting first crop of crystals was filtered and set aside. The supernatant was concentrated using a stream of nitrogen and a second crop of crystals was collected. The first and second crops were combined and dried in a vacuum oven overnight to give 5.4 g of SP-36302 as an off-white solid. Identification was made from NMR and HPLC diode-array data. Yield from plant material was 0.1%

Scheme 3

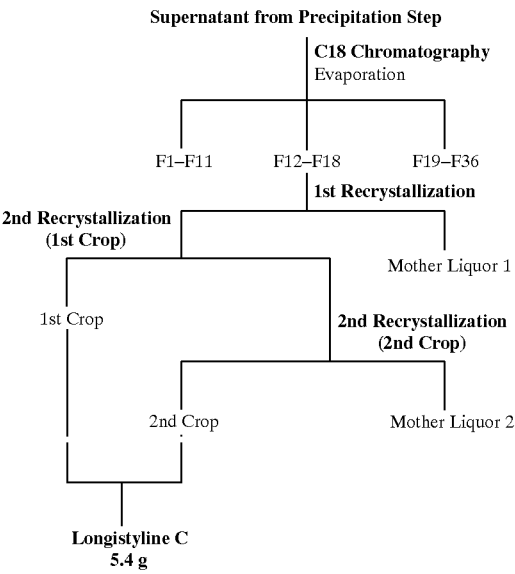

Structure Elucidation of the Stilbenoid Compounds

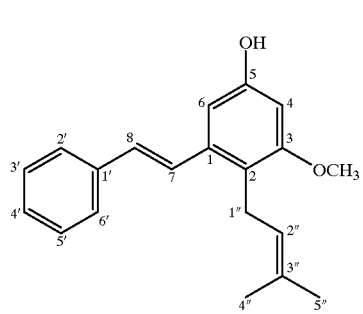

Longistyline C

Longistyline C was isolated previously from *Lonchocarpus violaceus* (*Lloydia*, 1977, 40, 201) and *Cajanus cajan* (Chung Ts'ao Yao, 1985, 18, 2). The molecular formula of Longistyline C was established as $C_{20}H_{22}O_2$ based on a peak in the HREIMS at m/z 294.1634 ($M^+$, $\Delta$4.8 ppm from calcd.). An IR spectrum of Longistyline C revealed absorbances at v ($cm^{-1}$): 3337, 2926, 1594, 1455, 1430, 1355, and 1316. The structure of Longistyline C was elucidated by careful interpretation of spectral data. Assignments were based on one and two-dimensional NMR experiments known to those skilled in the art of structure elucidation and included $^1$H NMR, $^{13}$C NMR, Heteronuclear Multiple Quantum Correlation (HMQC), and Heteronuclear Multiple Bond Correlation (HMBC). Values for the $^1$H NMR and $^{13}$C NMR chemical shifts of SP-36302 are given in the table below. Long range proton-carbon correlations observed in the HMBC spectrum are also listed.

NMR Data for Longistyline C

Spectra obtained in $CDCl_3$ $^{13}$C NMR @ 100 MHz: $\delta$; $^1$H NMR @ 400 MHz: $\delta$, integral, multiplicity, J

| Position | $^{13}$C NMR | $^1$H NMR | HMBC Correlations |
|---|---|---|---|
| 1 | 137.9 | — | |
| 2 | 121.0 | — | |
| 3 | 158.5 | — | |
| 4 | 98.5 | 6.38 1 H, d 2.8 Hz | C-2, C-3, C-5, C-6 |
| 5 | 154.3 | — | |
| 6 | 104.1 | 6.70 1 H, d 2.8 Hz | C-2, C-4, C-5, C-7 |
| 7 | 126.4 | 7.33 1 H, d 16 Hz | C-1', C-2, C-6 |
| 8 | 130.5 | 6.94 1 H, d 16 Hz | C-1, C-2' (C-6') |
| 1' | 137.5 | — | |
| 2'/6' | 126.5 | 7.49 2 H, m | C-8, C-4' |
| 3'/5' | 128.6 | 7.37 2 H, m | C-1' |
| 4' | 127.6 | 7.27 1 H, m | C-2' (C-6') |
| 3-OCH$_3$ | 55.7 | 3.81 3 H, s | C-3 |
| 1" | 24.4 | 3.43 2 H, d 7 Hz | C-1, C-2, C-3, C-2", C-3" |
| 2" | 123.4 | 5.12 1 H, t 7 Hz | C-4", C-5" |
| 3" | 130.9 | — | |
| 4" | 17.9 | 1.81 3 H, s | C-2", C-3", C-5" |
| 5" | 25.7 | 1.69 3 H, s | C-2", C-3", C-4" |

6.1.3.2 Longistyline A-2-carboxylic Acid (Compound A)

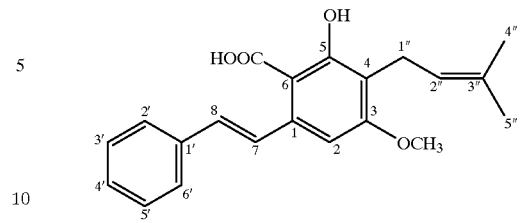

Compound A was reported previously from *Cajanus cajan* (Cooksey, et al., *Phytochemistry*, 1982, 21, 2935). Compound A was determined to have a molecular formula of $C_{21}H_{22}O_4$ based on the presence of a peak at m/z 337.1473 ($\Delta$ 9.9 ppm from calcd.) in the HRFABMS corresponding to $[M-H]^-$. The IR spectrum of Compound A showed absorbances at v ($cm^{-1}$): 3422, 2968, 1702, 1629, 1451, 1277, 1170, and 1117. The structure of Compound A was elucidated through careful examination of the spectral data. Values for the $^1$H NMR and $^{13}$C NMR chemical shifts of Compound A are given in the table below. Long range proton-carbon correlations observed in the HMBC spectrum are also listed.

NMR Data for Compound A

Spectra obtained in $CDCl_3$ $^{13}$C NMR@100 MHz: $\delta$; $^1$H NMR@400 MHz: $\delta$, integral, multiplicity, J

| Position | $^{13}$C NMR | $^1$H NMR | HMBC Correlations |
|---|---|---|---|
| 1 | 141.9 | — | |
| 2 | 103.3 | 6.67 1 H, s | C-1", C-1, C-3, C-4, C-6, C-7, 6-COOH |
| 3 | 162.4 | — | |
| 4 | 116.7 | — | |
| 5 | 162.2 | — | |
| 6 | 103.1 | — | |
| 7 | 130.4 | 7.87 1 H, d 16 Hz | C-1', C-1, C-2, C-6, C-8 |
| 8 | 130.7 | 6.84 1 H, d 16 Hz | C-1, C-7, C-1', C-2' (C-6') |
| 6-COOH | 175.7 | 4.70 1 H, br s | |
| 3-OCH$_3$ | 55.7 | 3.96 3 H, s | C-3 |
| 5-OH | — | 11.58 1 H, s | C-4, C-5, C-6, |
| 1' | 137.3 | — | |
| 2'/6' | 126.8 | 7.55 2 H, m | C-8, C-4' |
| 3'/5' | 128.7 | 7.40 2 H, m | C-1' |
| 4' | 127.8 | 7.30 1 H, m | C-2' (C-6') |
| 1" | 22.1 | 3.39 2 H, d 7 Hz | C-3, C-4, C-2", C-3" |
| 2" | 121.9 | 5.23 1 H, t 7 Hz | C-1", C-4", C-5" |
| 3" | 132.0 | — | |
| 4" | 17.8 | 1.81 3 H, s | C-2", C-3", C-5" |
| 5" | 25.8 | 1.70 3 H, s | C-2", C-3", C-4" |

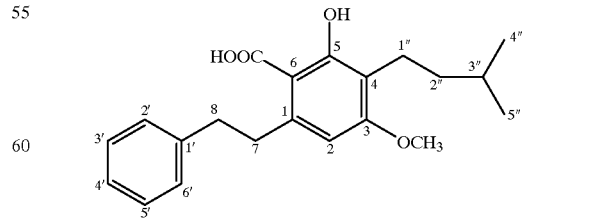

Compound I

Compound I was prepared by hydrogenation of Compound A. The molecular formula of Compound I was determined to be $C_{21}H_{26}O_4$ based on a peak in the HREIMS at m/z 342.1834 (M+, Δ 0.89 ppm from calcd.). The IR spectrum of Compound I showed absorbances at ν (cm$^{-1}$): 3398, 2951, 1609, 1457, 1271, and 1140. The structure of Compound I was elucidated through careful examination of the spectral data. Values for the $^1$H NMR and $^{13}$C NMR chemical shifts of Compound I, along with the long range proton-carbon correlations, are given in the table below.
NMR Data for Compound I
Spectra obtained in CDCl$_3$
$^{13}$C NMR@100 MHz: δ, $^1$H NMR@400 MHz: δ, integral, multiplicity, J

| Position | $^{13}$C NMR | $^1$H NMR | HMBC Correlations |
|---|---|---|---|
| 1 | 145.3 | — | |
| 2 | 106.4 | 6.21 1 H, s | C-3, C-4, C-6, C-7, 6-COOH |
| 3 | 162.3 | — | |
| 4 | 116.8 | — | |
| 5 | 163.0 | — | |
| 6 | 103.5 | — | |
| 7 | 39.2 | 3.27 2 H, m | C-1', C-1, C-2, C-6, C-8 |
| 8 | 38.2 | 2.94 2 H, m | C-1, C-7, C-1', C-2' (C-6') |
| 6-COOH | 175.4 | — | |
| 3-OCH$_3$ | 55.5 | 3.79 3 H, s | C-3 |
| 5-OH | — | 11.62 1 H, s | C-4, C-5, C-6, |
| 1' | 141.9 | — | |
| 2'/6' | 128.5 | 7.21 2 H, m | C-4', C-8 |
| 3'/5' | 128.3 | 7.31 2 H, m | C-1', C-2' (C-6') |
| 4' | 125.9 | 7.22 1 H, m | |
| 1" | 20.7 | 2.57 2 H, m | C-3, C-4, C-5, C-2", C-3" |
| 2" | 37.9 | 1.38 2 H, m | C-4, C-1", C-3", C-4", C-5" |
| 3" | 28.3 | 1.60 1 H, m | C-1", C-4", C-5" |
| 4" | 22.6 | 0.97 3 H, s | C-2", C-3", C-5" |
| 5" | 22.6 | 0.95 3 H, s | C-2", C-3", C-4" |

In vivo Hypotriglyceridemic Activity of the Stilbenoid of Formula (I)

This example illustrates the effectiveness of the stilbenoids of formula (I) in reducing serum triglyceride levels in fat-fed STZ treated male Sprague Dawley rats, i.e., an art-recognized model of hypertriglyceridemia.

A representative sampling of stilbenoid analogues were tested in the in vivo rat model described below.
In vivo Experiments 1–4, General The following experiments are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention as hereinafter claimed.

This example illustrates the effectiveness of the stilbenoids of formula (I), e.g. longistyline A-2-carboxylic acid (Compound A) in reducing serum triglyceride levels in fat fed, STZ treated male Sprague Dawley rats, i.e., an art recognized model of hypertriglyceridemia.
Materials and Methods Male Sprague Dawley rats arrival from Charles River Laboratories, Hollister, Calif., were fed a high fat (20% by weight) diet (TD 78463) obtained from Harlan Teklad, Madison, Wis., which was stored at 4° C. prior to use. Administration of a high fed diet is a well-known method of inducing hypertriglyceridemia in rats.

Compound A was obtained by the procedures described above in Section 6.1. GELUCIRE™ 44/14 vehicle was obtained from Gattefossé Corp., Westwood, N.J.; triglyceride standard and reagent were obtained from Sigma Chemical Company, St. Louis, Mo.

GELUCIRE™ vehicle was warmed to 48–50° C. prior to addition of the appropriate amount of Compound A. The resulting mixture was vortexed and then sonicated at 48–50° C. until the Compound A was completely dissolved. Prior to administration GELUCIRE™ vehicle and Compound A/vehicle were kept in a water bath at 48–50° C. to prevent solidification.

Compound A formulations were prepared fresh daily. The appropriate amount of Compound A in GELUCIRE™ was administered by oral gavage at a volume of 2.5 ml/kg of body weight. Animals were fasted at 8:00 am each day.

Blood samples from tail snips bleeds were collected six hours after the dose on day one, and three (3) and six (6) hours after the administration of the dose on days 2 through 4 into M brand (Becton Dickinson, Franklin Lakes, N.J.) serum separator tubes, and centrifuged at 12,000 rpm for 10 minutes. Serum was removed and triglyceride levels were measured using enzymatic calorimetric methods (M. W. McGowan, et al., Clin. Chem. 29, 538 (1983) and P Trinder, Ann. Clin. Biochem. 6, 24 (1969)) using Sigma Diagnostic Kits, Sigma Chemical Company, St. Louis, Mo.

Triglyceride levels are expressed as the mean ±SEM. Data were analyzed by one-way analysis of variance (ANOVA), followed by post-hoc Fisher's protected least squares difference (PLSD) tests. Statistical significance was defined as $p<0.05$.

After administering the high fat diet for at least two weeks to the rats, basal (pre-treatment) blood samples from tail snip bleeds were collected, and serum triglyceride (TG) levels were measured. A computer sorting program was used to distribute the animals into groups having equivalent initial mean TG levels. Subsequent treatment with vehicle alone or Compound C in GELUCIRE™ vehicle was once per day (q.d.).

Figure 2:
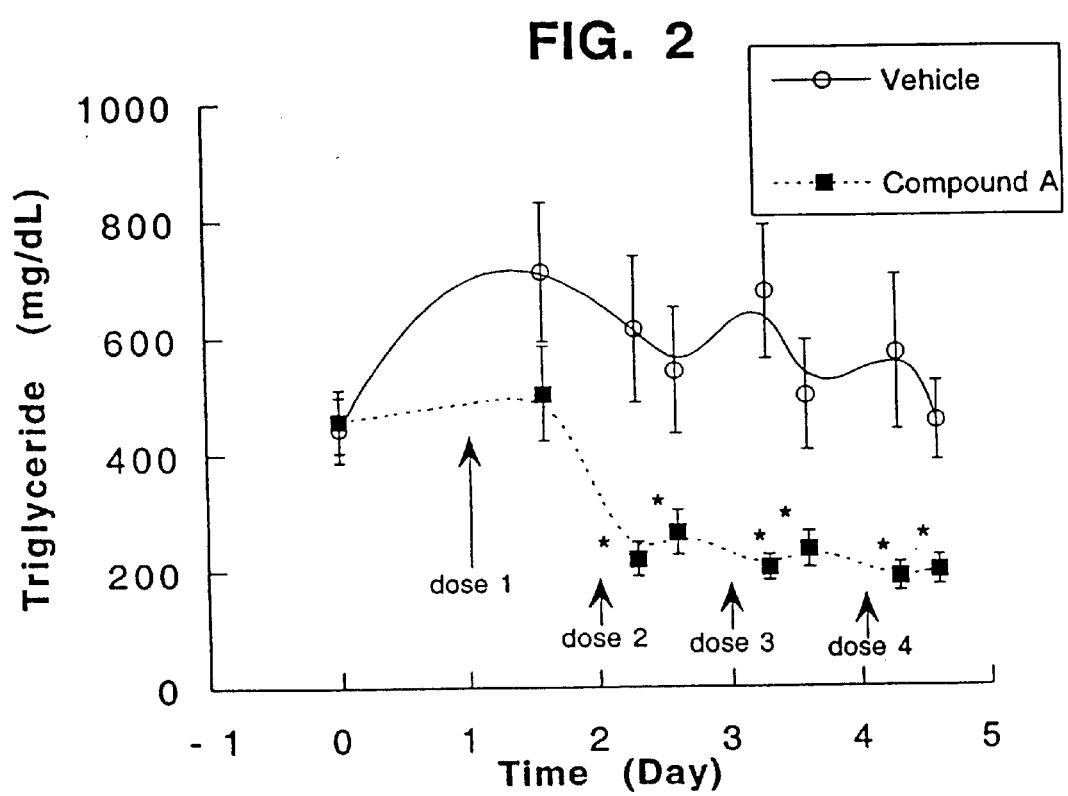
FIG. 2 is a line graph showing the mean triglyceride levels (mg/dL) in Fat fed, STZ treated rats administered with GELUCIRE™ vehicle only; and 3-hydroxy-4-(3-methyl-2-butenyl)-5-methoxystilbene-2-carboxylic acid (Compound A). -O- represents vehicle; and -■- represents Compound A administered at 250 mg/kg q.d. Animals were administered the vehicle and compounds at 24, 48, 72 and 96 h, and serum triglyceride levels were measured at 0, 30, 51, 54, 75 and 80 hours after the oral administration. All data points N=8. *P<0.05 (analysis of variance (ANOVA), one factor).

Blood samples on each day were collected, by tail snip, six hours after the daily dose. On days two through 4, an additional blood sample was collected each day, three hours after the daily dose. Serum was collected from each blood sample, and triglyceride levels were measured.
Results Serum triglyceride (TG) levels observed over the course of treatment with GELUCIRE™ vehicle or Compound A (250 mg/kg body weight, q.d.) in GELUCIRE™ vehicle are shown in FIG. 2. At each of the time points, TG levels for animals administered Compound A were significantly lower ($p<0.05$) than those obtained after administration of vehicle only. When compared at individual sampling times, the data indicate that the treatment groups that received 250 mg/kg of body weight, q.d., of Compound A, had mean TG levels that were significantly lower than those of the GELUCIRE™ vehicle treatment group from day 2 through the end of treatment.

Figure 3:
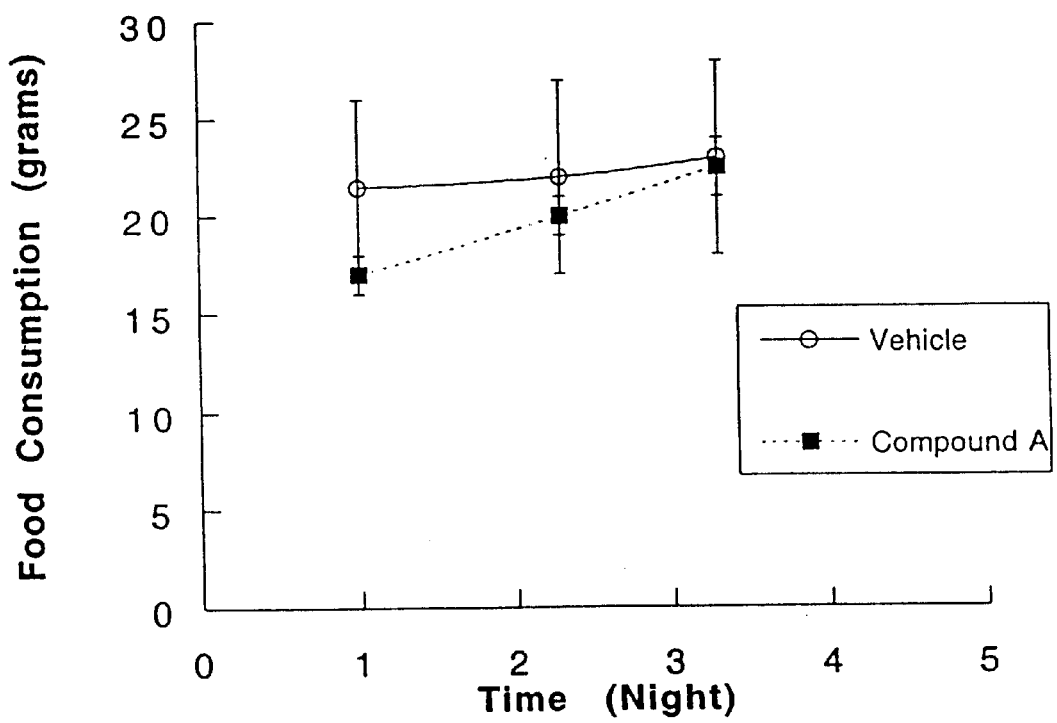
FIG. 3 is a line graph showing the mean body weight (mg) in fat fed, STZ treated rats administered with GELUCIRE™ vehicle only; and 3-hydroxy-4-(3-methyl-2-butenyl)-5-methoxystilbene-2-carboxylic acid (Compound A). -O- represents vehicle; and -■- represents Compound A administered at 250 mg/kg q.d. Animals were administered the vehicle and compounds at 24, 48, 72 and 96 h, and serum triglyceride levels were measured at 0, 30, 51, 54, 75 and 80 hours after the oral administration. All data points N=8. *P<0.05 (analysis of variance (ANOVA), one factor).
Figure 4:
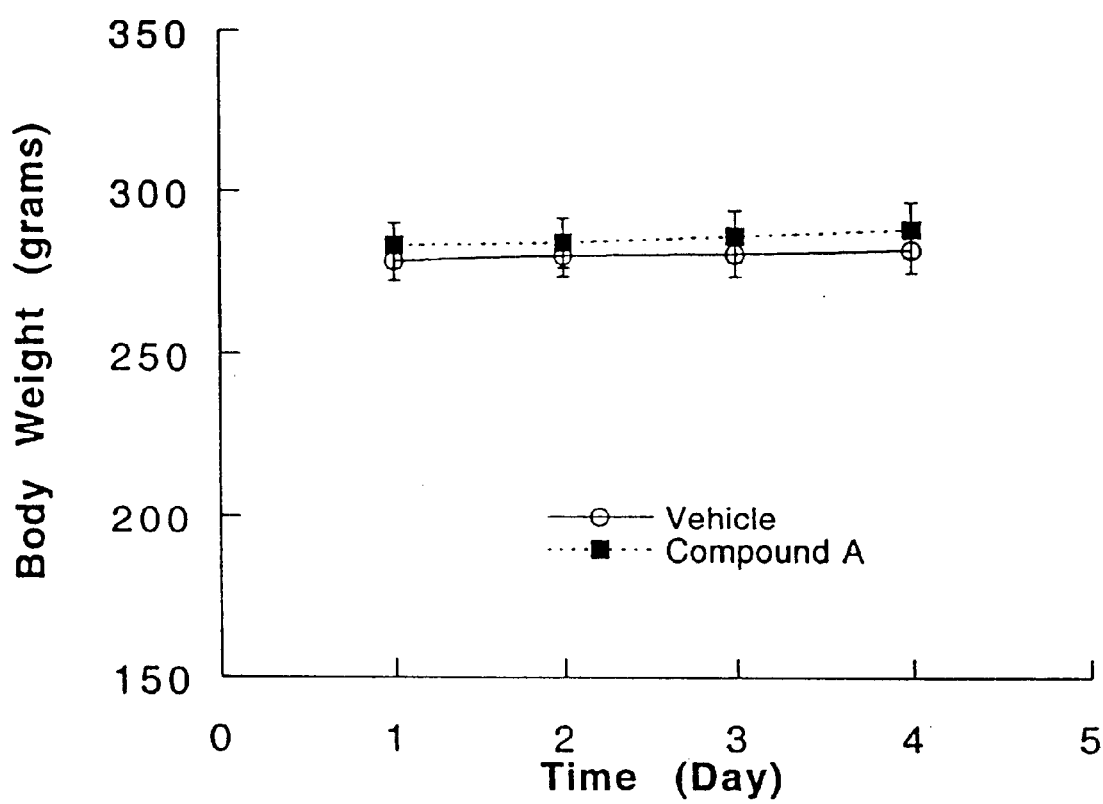
FIG. 4 is a line graph showing the mean food consumption (mg) in fat fed, STZ treated rats administered with GELUCIRE™ vehicle only; and 3-hydroxy-4-(3-methyl-2-butenyl)-5-methoxystilbene-2-carboxylic acid (Compound A). -O- represents vehicle; and -■- represents Compound A administered at 250 mg/kg q.d. Animals were administered the vehicle and compounds at 24, 48, 72 and 96 h, and serum triglyceride levels were measured at 0, 30, 51, 54, 75 and 80 hours after the oral administration. All data points N=8. *P<0.05 (analysis of variance (ANOVA), one factor).

Daily mean body weights are shown in FIG. 3. The gain in rat body weight over the course of treatment was normal and similar among the treatment groups and it does not appear that there was any biologically significant difference in body weight. The daily mean food consumption are shown in FIG. 4. The food intake was not effected by the treatments.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims.

All publications cited herein are incorporated by reference in their entirety.

What is claimed is:

1. A method of supplementing the diet of a mammal suffering from elevated blood triglyceride levels comprising administering to a mammal a dietary composition comprising a carrier and a hypotriglyceridemically effective amount of an isolated compound, or a pharmaceutically acceptable salt thereof, having the formula:

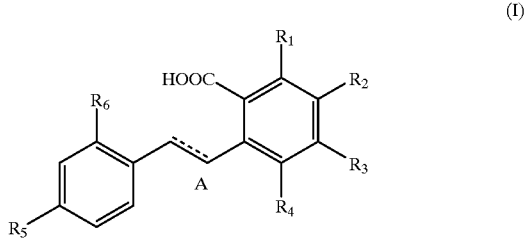

(I)

wherein,
- A is a bond selected from the group consisting of a single bond and a double bond in trans conformation;
- $R_1$ and $R_3$ are independently selected from the group consisting of H, OH, and $C_{1-6}$alkoxy;
- $R_2$ and $R_4$ are independently selected from the group consisting of H, $C_{1-11}$alkyl, $C_{2-11}$alkenyl, and $C_{2-11}$alkynyl;
- $R_5$ and $R_6$ are independently selected from the group consisting of H, OH, and $C_{1-6}$alkoxy; wherein said hypotriglyceridemically effective amount of said isolated compound is about 1 to about 1000 milligrams/kilogram of an intended subject, said subject being a mammal.

2. The method of claim 1, wherein said mammal has type I diabetes.

3. The method of claim 1, wherein said mammal has type II diabetes.

4. The method of claim 1, wherein said mammal is suffering from obesity.

5. The method of claim 1, wherein said mammal has atherosclerotic cardiovascular disease.

6. The method of claim 1, wherein said hypotriglyceridemically effective amount of said compound is about 1 to about 1000 mg/kg/day.

7. The method of claim 6, wherein said hypotriglyceridemically effective amount of said compound is between about 50 to about 350 mg/kg/day.

8. The method of claim 1, wherein said composition is administered orally.

9. The method of claim 1, wherein said compound is isolated from *Cajanus cajan*.

10. The method of claim 1, wherein said dietary composition is in the form of a nutrition bar, a cereal, an energy bar, a soup, or a pet food.

11. The method of claim 1, wherein said carrier is selected from the group consisting of a dried bakery product, wheat flour, rice flour, oat flour, corn flour, soy flour, wheat bran, rice bran, oat bran, corn bran, wheat middlings, whole ground wheat, corn gluten meal, whole ground corn, soybean meal, barley, sorghum, meat and bone meals, poultry meal, fish meal and dry pet food.

12. The method of claim 1, wherein said compound is selected from the group consisting of:

(A) 3-hydroxy-4-(3-methyl-2-butenyl)-5-methoxystilbene-2-carboxylic acid;

(B) 3-hydroxy-6-(3-methyl-2-butenyl)-5-methoxystilbene-2-carboxylic acid;

(C) 4-(3-methyl-2-butenyl)-3,5-dimethoxystilbene-2-carboxylic acid;

(D) 6-(3-methyl-2-butenyl)-3,5-dimethoxystilbene-2-carboxylic acid;

(E) 3,4'-dihydroxystilbene-2-carboxylic acid;

(F) 3,5-dihydroxystilbene-2-carboxylic acid;

(G) 3,4'-dihydroxybibenzyl-2-carboxylic acid (Compound G);

(H) 3,5-dihydroxy-4-(3-methyl-2-butenyl)bibenzyl-2-carboxylic acid (Compound H); and (I) 3,5-dihydroxy-4-(3-methyl-2-butenyl)bibenzyl-2-carboxylic acid.

* * * * *